United States Patent [19]

Evans et al.

[11] Plant 4,839

[45] Apr. 20, 1982

[54] SPUR-TYPE RED DELICIOUS APPLE TREE

[75] Inventors: William G. Evans; Don R. Snipes, both of Yakima, Wash.

[73] Assignee: Van Well Nursery, Inc., Wenatchee, Wash.

[21] Appl. No.: 148,249

[22] Filed: May 9, 1980

[51] Int. Cl.[3] ..... A01H 5/00

[52] U.S. Cl. ..... Plt./35

[58] Field of Search ..... Plt./35

*Primary Examiner*—James R. Feyrer

*Attorney, Agent, or Firm*—Christensen, O'Connor, Johnson & Kindness

[57] ABSTRACT

A new and distinct variety of spur-type Red Delicious tree with the productivity and growth characteristics of its parent Oregon Spur and with fruit and stem coloring with blush red formation nearest resembling the color of Early Red One, U.S. Plant Pat. No. 3,556, but approximately 15 days ahead of the initiation of coloration and ahead of the attainment of full coloration of Early Red One.

1 Drawing Figure

BACKGROUND OF THE INVENTION

The present new and distinct variety of Red Delicious Apple tree was discovered originating as a sport limb mutation on an Oregon Spur Red Delicious tree, U.S. Plant Pat. No. 2,816, in the discoverer's orchard in Yakima County, Wash. It has been reproduced in the discoverer's orchard through the third generation by budding and grafting and also in the Van Well Nursery orchard in Wenatchee, Wash., by the same method. Each successive generation has proved true to the original sport limb mutation so as to establish the genetic stability of this new variety.

The new variety of Red Delicious tree has been grown alongside other varieties that are believed to be the nearest similar to it, including Early Red One Delicious, U.S. Plant Pat. No. 3,556, Oregon Spur Delicious, U.S. Plant Pat. No. 2,816, and Bisbee Delicious, U.S. Plant Pat. No. 1,565. The new variety clearly differs from its parent, Oregon Spur, in that it begins to color with a blush contrasting with the striped color pattern of its parent. While mature fruit of the new variety has the appearance of that of Early Red One, the latter is not a spur-type tree. The present new variety starts to show fruit color approximately two weeks earlier than Early Red One or any other Red Delicious tree of which applicant is aware, and it also reaches full color in advance of all other Red Delicious trees by about the same lead period.

The new variety also shares with Early Red One the characteristic of developing a red stem color which it retains until the fully ripened fruit is ready for harvest. However, like the fruit itself, the stem color forms in the new variety some two weeks ahead of the appearance of stem color of Early Red One, namely, in the case of the new variety, approximately 15 days after bloom in the Yakima valley area.

By way of further comparisons, Oregon Spur obtains its full color, a dark red color, in the Yakima area some 30 days after full color is reached by the new variety. A similar comparison applies to Bisbee. As stated previously, at maturity the fruit color most nearly resembles that of Early Red One, a standard or nonspur-type tree.

The new variety is also distinguishable from Red Chief, U.S. Plant Pat. No. 3,578, and from Flanagan, U.S. Plant Pat. No. 3,557, in that these latter two produce apples which are colored with a striped pattern whereas the new variety fruit colors with a blush.

BRIEF DESCRIPTION OF THE DRAWING

The drawing consists of a photograph showing the fruit of the new variety in the middle of the picture, that of "Bisbee" at the left and that of "Oregon Spur" at the right, all three picked at the same time from about 30 days after bloom in the Yakima valley area.

DETAILED DESCRIPTION OF THE APPLE TREE

Tree: Medium, upright, dense, slow growing, with spur-type growth characteristics. Very productive, typical of other spur-type Red Delicious trees such as U.S. Plant Pat. No. 2,816.

Leaves: Comparable to those of other spur-type Red Delicious trees.

Flower: Similar to its parent Oregon Spur, namely, white with pink tinge and blooming in the Yakima valley area from April 27 to May 7.

Fruit: Fruit starts to color with a red blush earlier than that of its parent (Oregon Spur) and Bisbee by about 30 days and earlier than Early Red One by about 15 days, the blush red color appearing on both the stem and the fruit itself initially and filling into a solid dark red color of fruit and stem with no stripe formation discernible, with full coloration occurring in advance of that of Oregon Spur and Bisbee by about 30 days and of Early Red One by about 15 days. Fruit matures at approximately the same time as that of its parent Oregon Spur. Final color is approximately blackish-red, plate XII, No. 67, tone K of *Ridgeway Color Standards and Nomenclature.*

Stem: Medium length similar to its parent Oregon Spur, i.e., approximately 1 to 1½ inches at maturity. Stem develops a red color at the same time as the fruit, namely, within 15 days after bloom. Stem color, natural red, Ridgeway plate XXXVII, No. 71 VRR, Color K.

We claim:

1. A new and distinct variety of spur-type Red Delicious tree, substantially as described and illustrated, with the productivity and growth characteristics of its parent Oregon Spur and with fruit and stem coloring with blush red formation nearest resembling the color of Early Red One, U.S. Plant Pat. No. 3,556, but approximately 15 days ahead of the initiation of coloration and ahead of the attainment of full coloration of Early Red One.

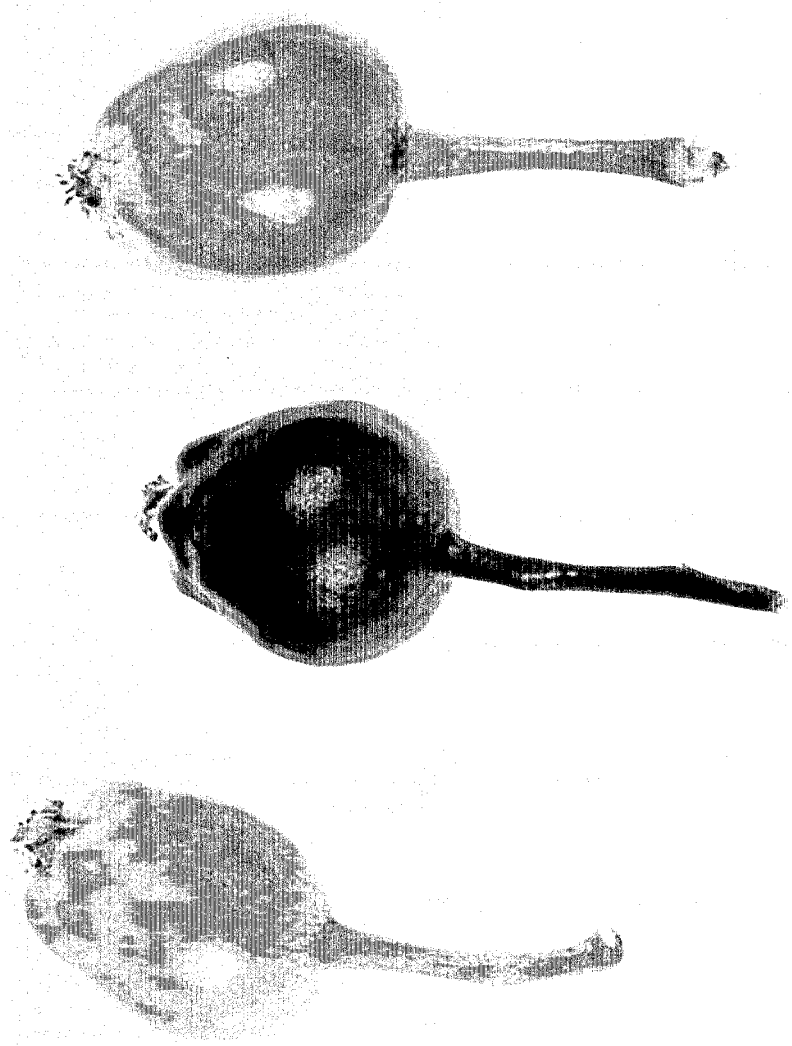

* * * * *